US00PP17487P2

(12) United States Plant Patent
Ackerman et al.

(10) Patent No.: US PP17,487 P2
(45) Date of Patent: Mar. 13, 2007

(54) STRAWBERRY PLANT NAMED 'PS-4634'

(50) Latin Name: *Fragaria ananassa*
Varietal Denomination: PS-4634

(75) Inventors: Stephen M. Ackerman, Salinas, CA (US); Steven D. Nelson, Watsonville, CA (US); Michael D. Nelson, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 0 days.

(21) Appl. No.: 11/221,869

(22) Filed: Sep. 9, 2005

(51) Int. Cl.
*A01H 5/00* (2006.01)

(52) U.S. Cl. ..... Plt./208
(58) Field of Classification Search ..... Plt./208
See application file for complete search history.

(56) References Cited

U.S. PATENT DOCUMENTS

PP9,903 P * 5/1997 Ackerman et al. ..... Plt./209
PP9,909 P * 6/1997 Ackerman et al. ..... Plt./209
PP10,780 P * 2/1999 Ackerman et al. ..... Plt./208

* cited by examiner

*Primary Examiner*—Wendy Haas
(74) *Attorney, Agent, or Firm*—Foley & Lardner LLP

(57) ABSTRACT

This invention relates to a new and distinct short-day variety of strawberry plant named 'PS-4634'. This new strawberry variety 'P-4634' is primarily adapted to the growing conditions of the central coast of California, and is primarily characterized by its large plant size, strong vigor rate, large foliage with medium to strong blistering and gloss, highly productive with fruit harvest beginning as early as late March in Salinas, Calif., producing upwards of 15% to 20% of its production by the end of May, and produced fruit is very large in size, light red in color, conical in shape with very good firmness and gloss.

4 Drawing Sheets

Latin name of the genus and species of the plant claimed: *Fragaria ananassa.*
Variety denomination: 'PS-4634'.

BACKGROUND OF THE INVENTION

The present invention relates to a new and distinct short-day strawberry variety designated as 'PS-4634'. This new variety is a result of a controlled cross made by the Inventors, Stephen M. Ackerman, Steven D. Nelson and Michael D. Nelson, in 1997 between strawberry variety designated 'PS-592' (patented, U.S. Plant Pat. No. 9,903) and strawberry variety designated 'PS-1031' (patented, U.S. Plant Pat. No. 9,909). The variety is botanically known as *Fragaria ananassa.*

The seedling resulting from the aforementioned cross was asexually propagated by stolons in a nursery located in Siskiyou County, Calif., and was subsequently selected by the Inventors from a controlled breeding plot near Salinas, Calif. in 1999. After its selection, the new variety was further asexually propagated by stolons in both Siskiyou County, Calif., and San Joaquin County, Calif. The new variety was extensively tested over the next several years in fruiting fields near Salinas, Calif. This propagation has demonstrated that the combination of traits disclosed herein as characterizing the new variety are fixed and remain true to type through successive generations of asexual reproduction.

BRIEF SUMMARY OF THE INVENTION

'PS-4634' is primarily adapted to the climate and growing conditions of the central coast of California. This region provides the necessary winter temperatures required for it to produce a strong vigorous plant and to remain in fruit production from April through November. The nearby Pacific Ocean provides the needed humidity and moderate temperatures to maintain fruit quality during the spring, summer and fall production months.

The following traits have been repeatedly observed and are determined to be unique characteristics of 'PS-4634', which in combination distinguish this strawberry plant as a new and distinct variety:

1. large plant size;
2. strong vigor rate;
3. large foliage with medium to strong blistering and gloss;
4. highly productive with fruit harvest beginning as early as late March in Salinas, Calif., producing upwards of 15% to 20% of its production by the end of May; and
5. produced fruit is very large in size, light red in color, conical in shape with very good firmness and gloss.

The strawberry varieties that are believed to be most closely related to the new strawberry variety 'PS-4634' are the parental strawberry variety 'PS-592' and the strawberry variety 'PS-1150' (patented, U.S. Plant Pat. No. 10,780).

In comparison to the similar strawberry varieties 'PS-592' and 'PS-1150', 'PS-4634' differs by the following combination of characteristics as described in Table 1:

TABLE 1

| Characteristic | 'PS-4634' | 'PS-592' (PP9,903) | 'PS-1150' (PP10,780) |
|---|---|---|---|
| Plant | | | |
| Size | large | large | medium-small |
| Stolon pubescence | medium-weak | medium | medium-strong |
| Foliage/Petioles | | | |
| Leaf size | medium-large | large | medium-small |
| Gloss | medium-strong | medium-strong | medium-weak |
| Blistering | medium-strong | medium-strong | medium-weak |
| Stipule anthocyanin coloration | strong | medium | absent or very weak |
| Stipule length | medium-long | long | medium |
| Fruit | | | |
| Size | large-very large | large | small |
| Flavor | very good | very good | good |
| Color | red-orange red | red-orange red | red |
| Band without achenes | narrow | absent or very narrow | absent or very narrow |
| Unevenness of surface | weak-medium | weak | absent or very weak |
| Attitude of calyx segments | spreading-reflexed | spreading-reflexed | spreading-collapsing |
| Skin firmness | strong | medium | strong |
| Inflorescences | | | |
| Position relative to foliage | level with | level with-beneath | above |
| Fruiting truss length | long | long | medium |
| Time of ripening | early | early | late |

For identification, a series of molecular markers have been determined for this new variety.

BRIEF DESCRIPTIONS OF THE DRAWINGS

The accompanying color photographs illustrate the overall appearance of typical specimens of the new strawberry variety, 'PS-4634' at various stages of development as true as reasonably possible with color reproductions of this type. Color in the photographs may differ slightly from the color value cited in the detailed botanical description which accurately describe the color of 'PS-4634'. The depicted plant and plant parts of the new strawberry variety 'PS-4634' were taken in Salinas, Calif., and are approximately 8 to 9 months old.

DETAILED BOTANICAL DESCRIPTION

Figure 1:
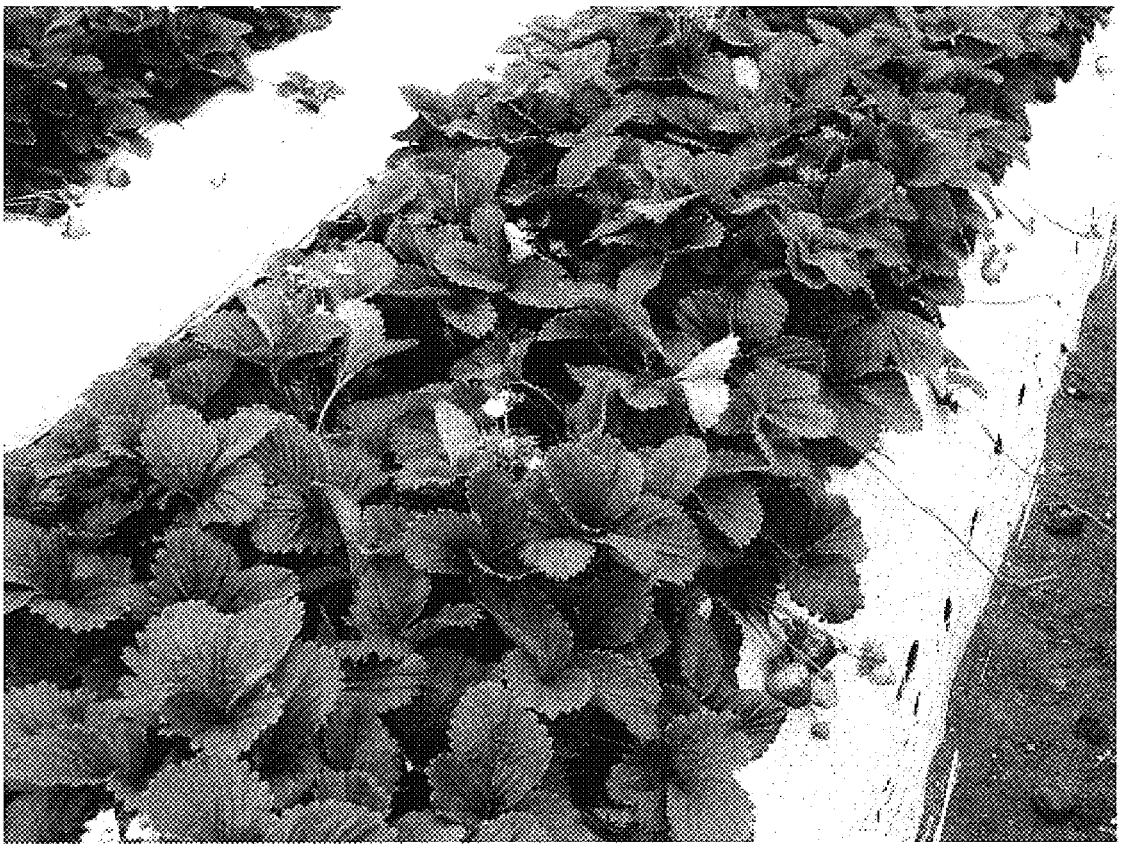
FIG. 1 shows typical fruiting field characteristics on Jun. 3, 2004.
Figure 2:
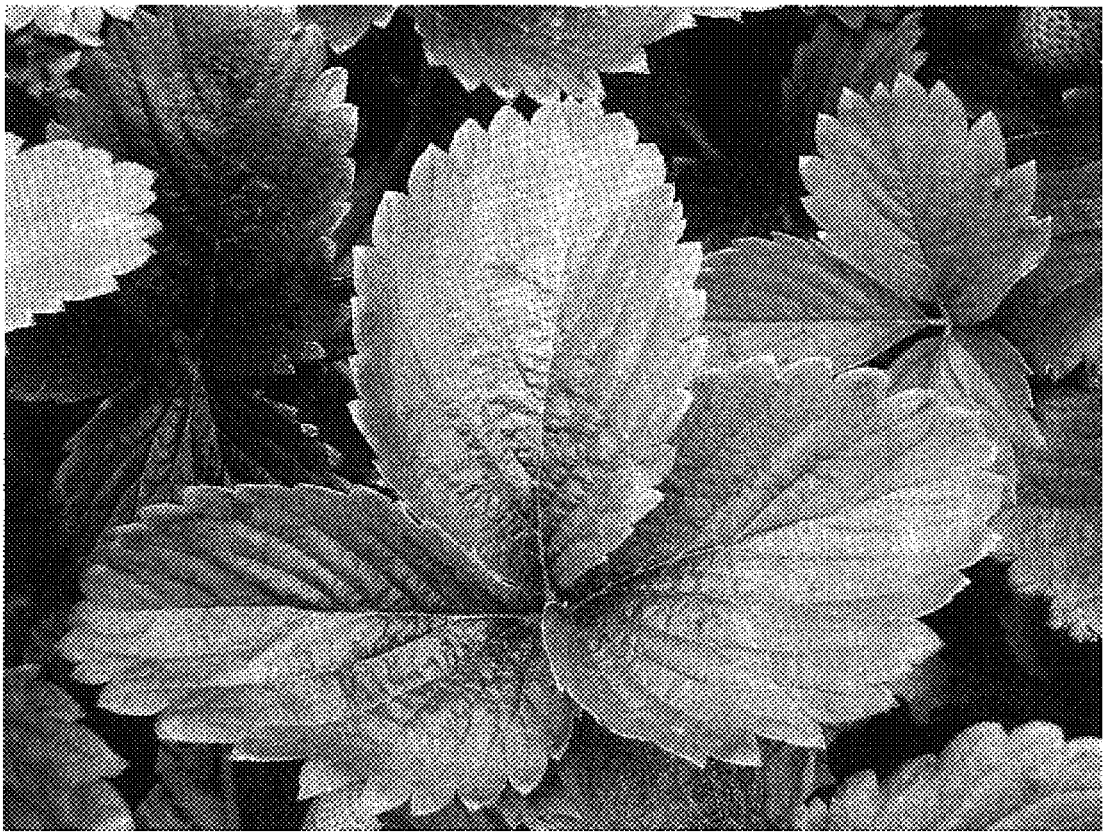
FIG. 2 shows a close-up view of a typical mature trifoliate on Jun. 3, 2004.
Figure 3:
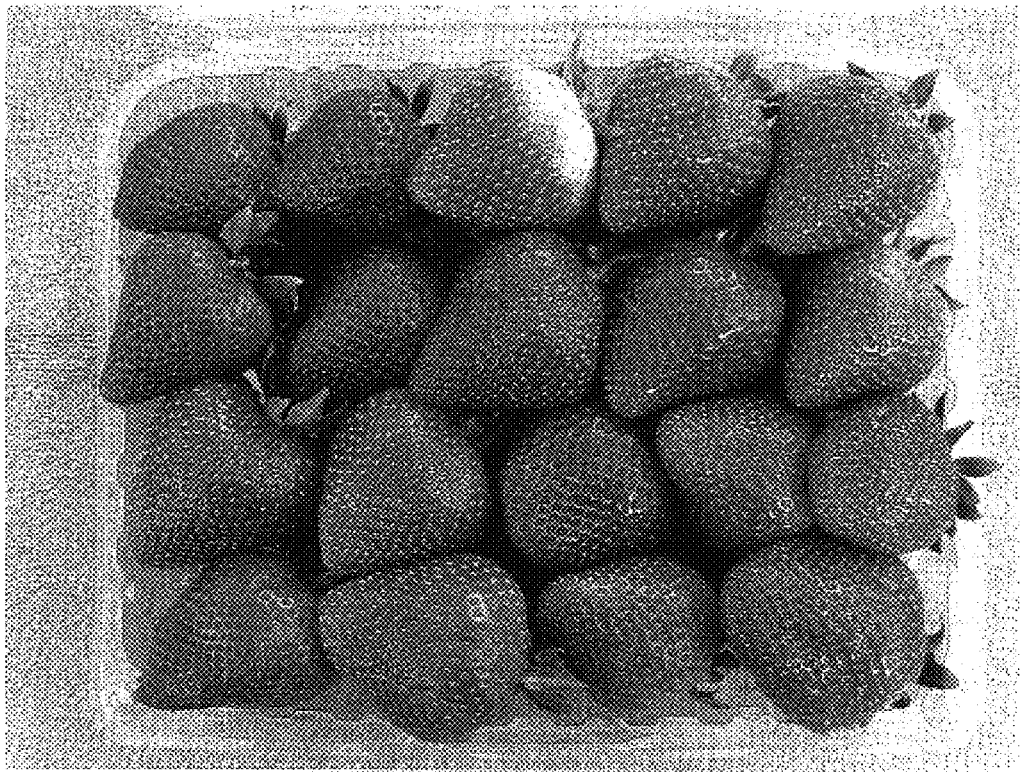
FIG. 3 shows a close-up view of fruit on Jul. 12, 2004.
Figure 4:
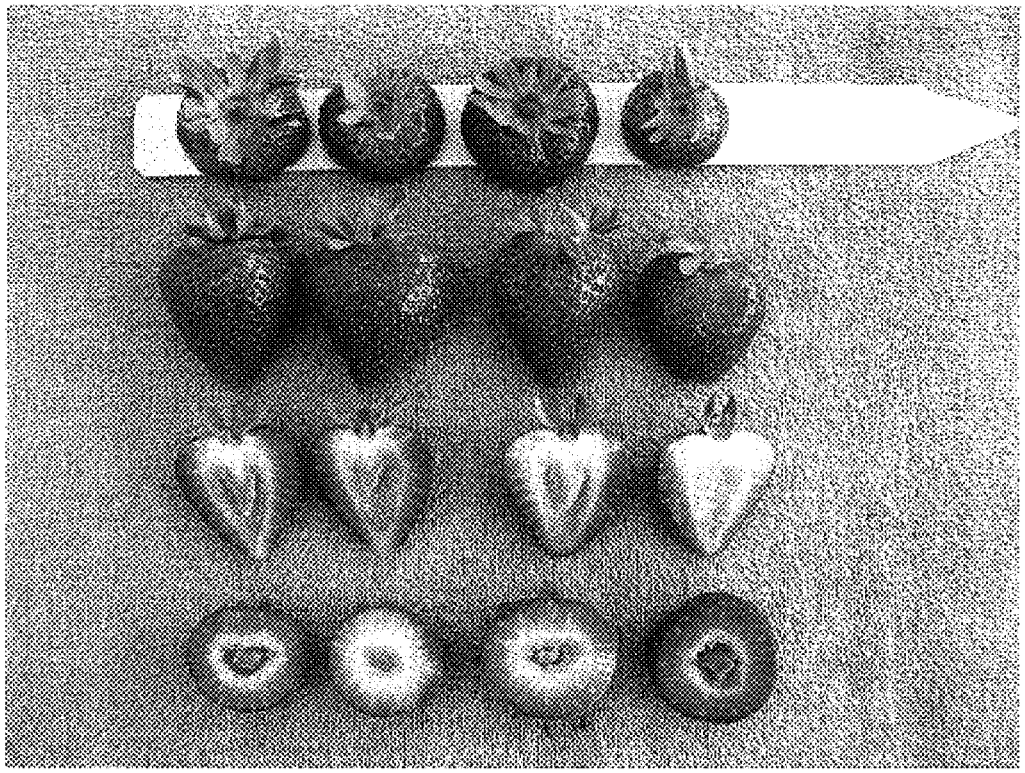
FIG. 4 shows typical internal and external fruit characteristics on Jul. 9, 2003.
Figure 5:
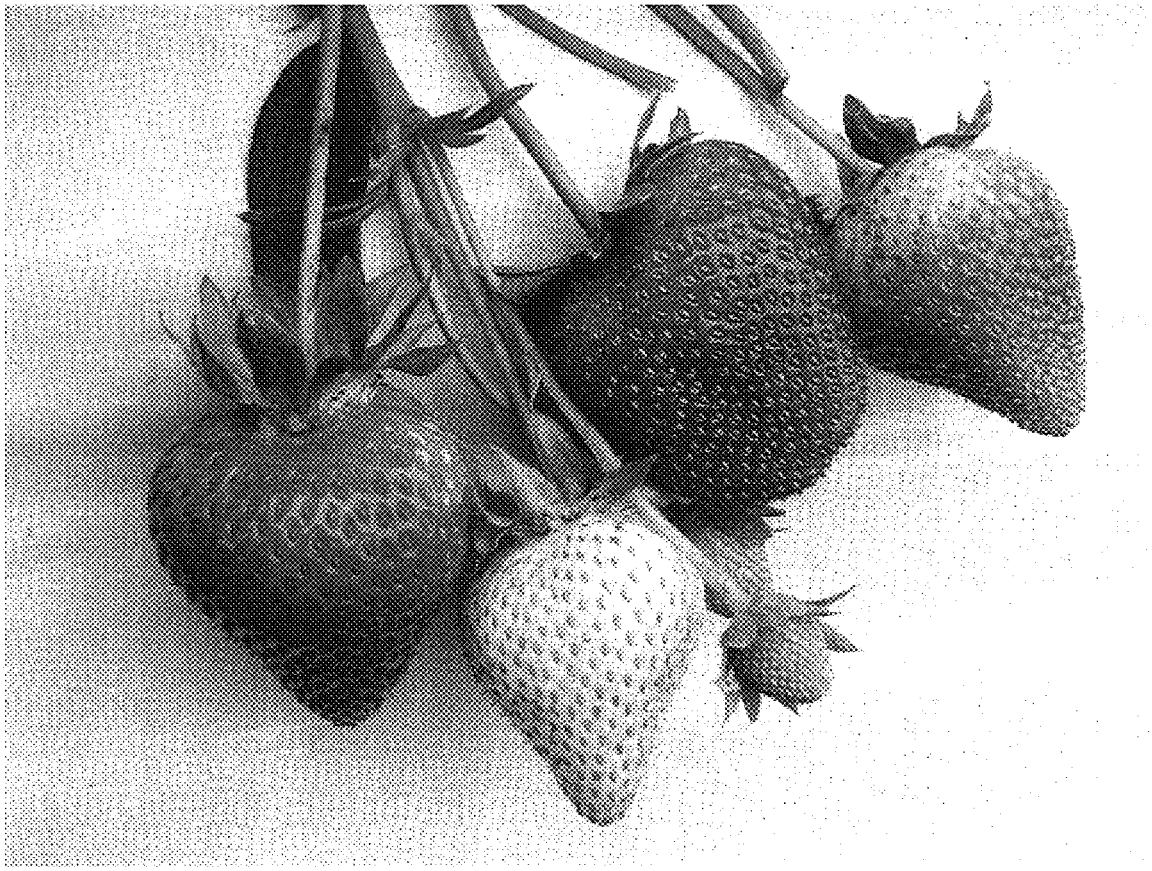
FIG. 5 shows typical mature and immature field fruit on Jun. 3, 2004.

'PS-4634' has not been observed under all possible environmental conditions. The characteristics of the new variety may vary in detail, depending upon variations in environmental factors, including weather (temperature, humidity and light intensity), day length, soil type and location.

The aforementioned photographs, together with the following description of the new strawberry variety 'PS-4634', unless otherwise noted, is based on observations taken during the 2004 growing season in Salinas, Calif. These measurements and ratings were taken from plants of 'PS-4634' dug from a high-elevation nursery located in Siskiyou County, Calif., during the middle of October 2003 and planted approximately 3 weeks later in Salinas, Calif. The approximate age of the observed plants is 8 to 9 months. Yield observations and fruit quality characteristics are averaged from three years of data collected from the 2002 through the 2004 growing seasons.

Color terminology follows the Munsell Book of Colors, Munsell Color, Baltimore, Md. (1976).

Fruit characteristics: Tables 2, 3 and 4 describe fruit, fruit production and fruit quality characteristics of 'PS-4634'. Fruit characteristics are taken from secondary fruit on a first year planting.

TABLE 2

2002–2004 market fruit yield and fruit size characteristics of 'PS-4634' with standards from Salinas, California.

| Cultivar | 2002–2004 Average April/May Yield GM/PL | 2002–2004 Average Total Yield GM/PL | 2002–2004 Average Fruit Size GRM |
|---|---|---|---|
| 'PS-4634' | 299 | 1829 | 24.5 |
| 'PS-592' | 282 | 1598 | 22.7 |
| 'PS-1150' | 154 | 1277 | 17.3 |

Fruit was harvested from April through November 2002–2004. The plants of 'PS-4634' were dug from a high elevation nursery (Macdoel, California) during the middle of October and planted approximately 3 weeks later in Salinas, California. 'PS-4634' is compared with standards dug and planted comparably.

TABLE 3

Comparison of 2002–2004 fruit quality characteristics, including flavor and soluble solids of 'PS-4634', with standards from Salinas, California.

| Character | 'PS-4634' | 'PS-592' | 'PS-1150' |
|---|---|---|---|
| Skin Firmness* | 8.3 | 7.8 | 8.5 |
| Fruit Appearance* | 7.9 | 7.8 | 8.2 |
| Fruit Gloss* | 8.4 | 8.3 | 8.5 |
| Flavor** | 3.1 | 3.2 | 2.7 |
| Soluble Solids*** | 7.4 | 9.2 | 7.8 |

*Results are averaged from 3 years of data collected from April through October 2002–2004. Ratings are based on a scale from 1–10; the higher the rating, the stronger the skin and more attractive and glossy the berry.
**Results are averaged from 3 years of data collected from April through October 2002–2004. Ratings are based on a scale from 1–5; the higher the rating the better the flavor.
***Results are averaged from 2 years of data collected from April through October 2003–2004. Soluble solid content is measured in percent Brix, with percent Brix being an indirect measurement of the sugar content in the fruit.

TABLE 4

Comparison of secondary fruit characteristics of 'PS-4634', with standards from Salinas, California, Jul. 13, 2004.

| Character | 'PS-4634' | 'PS-592' | 'PS-1150' |
|---|---|---|---|
| Munsell Color Range Mature Fruit | 7.5R 3/12 to 7.5R 4/12 | 7.5R 3/12 to 7.5R 4/12 | 7.5R 4/10 to 7.5R 3/8 |
| Fruit Length mean (cm) | 4.9 | 4.7 | 4.1 |
| Fruit Width mean (cm) | 4.3 | 4.5 | 3.8 |

TABLE 4-continued

Comparison of secondary fruit characteristics of 'PS-4634', with standards from Salinas, California, Jul. 13, 2004.

| Character | 'PS-4634' | 'PS-592' | 'PS-1150' |
|---|---|---|---|
| Fruit Length/ Width Ratio | 1.14 | 1.04 | 1.09 |
| Calyx Diameter mean (cm) | 4.4 | 4.7 | 4.4 |
| No. Sepals/ Berry | 12.9 | 13.3 | 12.9 |

Fruit:

*Ratio of length/width.*—Slightly longer than broad.
*Size.*—Large to very large.
*Predominant shape.*—Conical.
*Difference in shapes between primary and secondary fruit.*—Moderate.
*Band without achenes.*—Narrow.
*Unevenness of surface.*—Medium to weak.
*Color of mature fruit.*—Red to orange red (7.5R 3/12 to 7.5R 4/12).
*Evenness of color.*—Slightly uneven to even.
*Glossiness.*—Strong.
*Insertion of achenes.*—Level with the surface.
*Insertion of calyx.*—Level with to in the basin.
*Attitude of the calyx segments.*—Spreading to reflexed.
*Size of calyx in relation to fruit diameter.*—Same size.
*Adherence of calyx (when fully ripe).*—Strong.
*Firmness of skin.*—Strong.
*Firmness of flesh.*—Medium.
*Color of flesh.*—Medium to light red (7.5R 5/10 to 7.5R 4/12).
*Distribution of red color of the flesh.*—Marginal and central.
*Hollow center.*—Strongly expressed.
*Receptacle color.*—Whitish (N 9.25/84.2%R to N 9/78.7%R).
*Achene color.*—Moderate red to moderate yellow (7.5R 3/8 to 5Y 6/8).
*Achene size.*—Medium to small (average 0.58 mg).
*Time of flowering (50% of plants at first flower).*—Early.
*Time of ripening (50% of plants with ripe fruit).*—Early.
*Type of bearing.*—Not remontant.

Plant characteristics: Table 5 describes plant characteristics of 'PS-4634'. Plant characteristics are taken from a fully mature mid season plant.

TABLE 5

Comparison of plant characteristics of 'PS-4634', with standards from Salinas, California, Aug. 13, 2004.

| Character | 'PS-4634' | 'PS-592' | 'PS-1150' |
|---|---|---|---|
| Plant Height mean (cm) | 31.1 | 33.5 | 26.5 |
| Plant Spread mean (cm) | 44.7 | 45.1 | 37.8 |

Plant:

*Size.*—Large.
*Habit.*—Globose.
*Density.*—Medium.
*Vigor.*—Strong.
*Stolons.*—Number: Medium to many. Anthocyanin coloration: Medium to weak 7.5R 4/8 to 7.5R 5/8). Thickness: Thick. Pubescence: Medium to weak.

Foliage characteristics: Table 6 describes foliage characteristics of 'PS-4634'. Foliage characteristics are taken from a fully mature tri-foliate during mid season.

TABLE 6

Comparison of leaf characteristics of 'PS-4634', with standards from Salinas, California, Jul. 1, 2004.

| Character | 'PS-4634' | 'PS-592' | 'PS-1150' |
|---|---|---|---|
| Munsell Color Range (upper surface) | 7.5GY 4/4 to 7.5GY 3/4 | 7.5GY 4/4 to 7.5GY 3/4 | 7.5GY 4/4 to 7.5GY 3/4 |
| Terminal Leaflet Length mean (cm) | 9.6 | 9.8 | 7.3 |
| Terminal Leaflet Width mean (cm) | 7.5 | 7.8 | 6.1 |
| Terminal Leaflet ratio (L/W) | 1.28 | 1.26 | 1.20 |
| Petiole Length mean (cm) | 23.4 | 24.0 | 18.7 |
| Petiole Width mean (mm) | 4.3 | 4.8 | 3.0 |
| Petiolule Length mean (mm) | 9.2 | 10.4 | 9.2 |
| Serrations/Leaf | 21.6 | 20.3 | 20.2 |
| Stipule Length mean (cm) | 1.9 | 2.3 | 1.6 |
| Stipule Width mean (cm) | 1.0 | 0.75 | 0.75 |

Foliage:

*Color of upper surface.*—Medium green, (7.5GY 4/4 to 7.5GY 3/4).
*Color of under side.*—Medium grey green, (5GY 5/4 to 5GY 6/4).
*Shape in cross section.*—Slightly concave to flat.
*Blistering.*—Medium to strong.
*Glossiness.*—Medium to strong.
*Number of leaflets/leaf.*—Three.
*Terminal leaflet.*—Size: Medium to large. Length/width ratio: Much longer than broad. Shape of base: Acute. Shape of incision of margins: Obtuse.
*Petiole.*—Pubescence: moderate to sparse.
*Anthocyanin coloration of stipule.*—Strong.
*Attitude of hairs.*—Slightly outwards.
*Frequency of bract leaflets.*—Occasionally to some (40–50%).

Flowers and inflorescences: Table 7 describes inflorescence and flower characteristics of 'PS-4634'. Inflorescence characteristics are taken from a fully mature plant while flower characteristics are taken from a secondary flower during mid season.

TABLE 7

Comparison of inflorescence and secondary flower characteristics of 'PS-4634', with standards from Salinas, California, Jul. 14, 2004.

| Character | 'PS-4634' | 'PS-592' | 'PS-1150' |
|---|---|---|---|
| Fruiting Truss Length * mean (cm) | 36.8 | 34.2 | 32.9 |
| Corolla Diameter mean (cm) | 3.7 | 3.6 | 3.1 |
| Calyx Diameter mean (cm) | 4.0 | 3.8 | 3.3 |
| Petal Length mean (cm) | 1.39 | 1.38 | 1.30 |

TABLE 7-continued

Comparison of inflorescence and secondary flower characteristics of 'PS-4634', with standards from Salinas, California, Jul. 14, 2004.

| Character | 'PS-4634' | 'PS-592' | 'PS-1150' |
|---|---|---|---|
| Petal Width mean (cm) | 1.39 | 1.41 | 1.24 |
| Petal L/W Ratio | 1.0 | .098 | 1.07 |
| Petals/Flower (mean) | 6.5 | 6.1 | 5.9 |
| Sepal Length mean (cm) | 1.28 | 1.47 | 1.15 |
| Sepal Width mean (cm) | 0.48 | 0.50 | 0.42 |
| Sepal L/W Ratio | 2.67 | 2.94 | 2.58 |
| Sepals/Flower (mean) | 12.75 | 12.3 | 11.9 |

* As measured from the base of the primary peduncle where it attaches to the crown of the plant to the furthest berry.

Inflorescence:

*Position relative to foliage.*—Level with.

*Pubescence.*—Medium to weak.

*Anthocyanins.*—Very light to none.

*Number of bract leaflets.*—Bracts occur on about 75% of the inflorescences.

*Size of bract leaflets.*—Medium.

*Fruiting truss length.*—36.8 cm.

Flowers:

*Color.*—White (N9.5/90.0%R to N9.25/84.2%R).

*Size.*—Large.

*Size of calyx relative to corolla.*—Larger.

*Relative position of petals.*—Overlapping.

*Petal length/width ratio.*—As long as broad.

Pest reactions: This new variety may not be resistant to any of the known insects, diseases or viruses common in California. It is known to be tolerant to the two-spotted spider mite, aphid and flower thrips when treated properly. It is also known to be moderately tolerant to grey fruit mold, powdery mildew and angular leaf spot yet susceptible to verticillium wilt. The susceptibility of the new variety to any of the virus complexes of California has not been determined.

We claim:

1. A new and distinct strawberry plant named 'PS-4634', as herein described and illustrated by the characteristics set forth above.

* * * * *